(12) United States Patent
Opawale et al.

(10) Patent No.: US 7,635,675 B2
(45) Date of Patent: Dec. 22, 2009

(54) MICRO-PARTICLE FATTY ACID SALT SOLID DOSAGE FORMULATIONS FOR THERAPEUTIC AGENTS

(75) Inventors: Foyeke Opawale, Raleigh, NC (US); Richard Soltero, Holly Springs, NC (US)

(73) Assignee: Biocon Limited (IN)

( * ) Notice: Subject to any disclaimer, the term of this patent is extended or adjusted under 35 U.S.C. 154(b) by 779 days.

(21) Appl. No.: 10/918,264

(22) Filed: Aug. 13, 2004

(65) Prior Publication Data

US 2005/0095216 A1 May 5, 2005

Related U.S. Application Data

(60) Provisional application No. 60/494,821, filed on Aug. 13, 2003.

(51) Int. Cl.
*A61K 9/14* (2006.01)
*A61K 9/20* (2006.01)
*A61K 9/26* (2006.01)
*A61K 9/16* (2006.01)
*A61K 38/02* (2006.01)
*A61K 38/16* (2006.01)
*A61K 38/23* (2006.01)
*A61K 38/28* (2006.01)
*C07K 17/00* (2006.01)
*C07K 17/02* (2006.01)
*C07K 17/08* (2006.01)

(52) U.S. Cl. ............... 514/12; 514/2; 514/3; 530/300; 530/345; 424/400; 424/407; 424/408; 424/409; 424/417; 424/420; 424/470

(58) Field of Classification Search ............... None
See application file for complete search history.

(56) References Cited

U.S. PATENT DOCUMENTS

| | | | |
|---|---|---|---|
| 3,957,662 A | 5/1976 | Sangekar et al. | |
| 4,179,337 A * | 12/1979 | Davis et al. | 435/181 |
| 4,310,543 A | 1/1982 | Gallo-Torres | |
| 4,439,420 A | 3/1984 | Mattei et al. | |
| 4,704,284 A | 11/1987 | Beatty | |
| 4,886,669 A * | 12/1989 | Ventouras | 424/469 |
| 4,900,734 A | 2/1990 | Maxson | |
| 5,028,432 A | 7/1991 | Chopra | |
| 5,140,021 A | 8/1992 | Maxson | |
| 5,147,655 A * | 9/1992 | Ibsen | 424/489 |
| 5,359,030 A | 10/1994 | Ekwuribe | |
| 5,405,877 A | 4/1995 | Greenwald | |
| 5,428,128 A * | 6/1995 | Mensi-Fattohi et al. | 530/302 |
| 5,518,998 A * | 5/1996 | Backstrom et al. | 514/3 |
| 5,532,002 A | 7/1996 | Story | |
| 5,536,508 A * | 7/1996 | Canal et al. | 424/501 |
| 5,567,422 A | 10/1996 | Greenwald | |
| 5,589,455 A | 12/1996 | Woo | |
| 5,612,460 A | 3/1997 | Zalipsky | |
| 5,637,749 A | 6/1997 | Greenwald | |
| 5,681,811 A | 10/1997 | Ekwuribe | |
| 5,736,542 A | 4/1998 | Henry | |
| 5,900,402 A | 5/1999 | Shorr | |
| 5,929,030 A | 7/1999 | Hamied | |
| 5,985,263 A | 11/1999 | Lee | |
| 6,057,139 A * | 5/2000 | Kulkarni et al. | 435/188 |
| 6,113,906 A | 9/2000 | Greenwald | |
| 6,200,602 B1 | 3/2001 | Watts | |
| 6,214,330 B1 | 4/2001 | Greenwald | |
| 6,251,427 B1 | 6/2001 | Kim | |
| 6,303,569 B1 | 10/2001 | Greenwald | |
| 6,486,124 B2 | 11/2002 | Olbrich | |
| 6,610,653 B1 | 8/2003 | Backström | |
| 6,627,219 B2 | 9/2003 | Hao | |
| 6,703,381 B1 | 3/2004 | Ekwuribe | |
| 6,770,625 B2 | 8/2004 | Soltero | |
| 6,858,580 B2 | 2/2005 | Ekwuribe | |
| 6,867,183 B2 | 3/2005 | Soltero | |
| 2002/0187536 A1 | 12/2002 | Kulkarni et al. | |
| 2003/0050228 A1* | 3/2003 | Ekwuribe et al. | 514/3 |
| 2003/0069170 A1* | 4/2003 | Soltero et al. | 514/2 |

FOREIGN PATENT DOCUMENTS

| | | |
|---|---|---|
| EP | 0230332 | 7/1987 |
| EP | 1331002 | 7/2003 |
| GB | 2391473 | 2/2004 |
| JP | 52156916 | 12/1977 |
| JP | 55153712 | 11/1980 |

(Continued)

OTHER PUBLICATIONS

Sakuma et al. Design of nanoparticles composed of graft copolymers for oral polypeptide delivery. Adv Drug Del Rev., 2001, vol. 47, pp. 21-37.
Motohiro Mishima, et al.; Studies on the Promoting Effects of Medium Chain Fatty Acid Salts on the Nasal Absorption of Insulin in Rats; J.Pharmacobio-Dynamics; 1987; pp. 624-631; vol. 10; No. 11.
Yoshinori Onuki, et al.; Formulation optimization of water-in-oil-water multiple emulsion for intestinal insulin delivery; Journal of Controlled Release; 2004; pp. 91-99; vol. 97, No. 1; Elsevier Science Publishers B.V. Amsterdam, NL.
Florence, A. T. The oral absorption of micro- and nonparticulates: neither exceptional nor unusual. Pharmaceut. Res., 1997, vol. 14, pp. 259-266.
Ermak et al. Uptake and transport of copolymer biodegradable microspheres by rabbit Pyere's patch M cells. Cel Tissue Res., 1995, vol. 279, pp. 433-436.

*Primary Examiner*—Andrew D Kosar
(74) *Attorney, Agent, or Firm*—Marianne Fuierer; Moore & Van Allen PLLC (57) ABSTRACT

Fatty acid salt particles having a size distribution wherein the particles are from about 1 to about 1,000 microns in diameter, use of the particles in pharmaceutical compositions, as well as methods of making and using the particles and compositions.

24 Claims, 8 Drawing Sheets

FOREIGN PATENT DOCUMENTS

| | | |
|---|---|---|
| JP | 56131514 | 10/1981 |
| JP | 57064609 | 4/1982 |
| JP | 57064610 | 4/1982 |
| JP | 57158719 | 9/1982 |
| JP | 58013508 | 1/1983 |
| JP | 58206515 | 12/1983 |
| JP | 59051223 | 3/1984 |
| JP | 59148735 | 8/1984 |
| JP | 59175433 | 10/1984 |
| JP | 60146825 | 8/1985 |
| JP | 60214735 | 10/1985 |
| JP | 60218318 | 11/1985 |
| JP | 61012632 | 1/1986 |
| JP | 61076416 | 4/1986 |
| JP | 61233625 | 10/1986 |
| JP | 62252723 | 11/1987 |
| JP | 63017821 | 1/1988 |
| JP | 1019018 | 1/1989 |
| JP | 1224315 | 9/1989 |
| JP | 2004712 | 1/1990 |
| JP | 2223526 | 9/1990 |
| JP | 3128322 | 5/1991 |
| JP | 3200715 | 9/1991 |
| JP | 3251536 | 11/1991 |
| JP | 7215883 | 8/1995 |
| JP | 8003074 | 1/1996 |
| JP | 10001436 | 1/1998 |
| JP | 10045629 | 2/1998 |
| JP | 2000095676 | 4/2000 |
| JP | 2000344661 | 12/2000 |
| JP | 63280017 | 11/2006 |
| WO | WO9004385 | 5/1990 |
| WO | WO9221348 | 12/1992 |
| WO | WO 94/08610 | 4/1994 |
| WO | WO9508983 | 4/1995 |
| WO | WO9908666 | 2/1999 |
| WO | WO9913739 | 3/1999 |
| WO | WO0053212 | 9/2000 |
| WO | WO0059482 | 10/2000 |
| WO | WO0239983 | 5/2002 |
| WO | WO03007920 | 1/2003 |
| WO | WO03017986 | 3/2003 |
| WO | WO2004047871 | 6/2004 |
| WO | WO2004054540 | 7/2004 |
| WO | WO2004073693 | 9/2004 |
| WO | WO2005004919 | 1/2005 |
| WO | WO2005079853 | 9/2005 |
| WO | WO2005089714 | 9/2005 |
| WO | WO2005105050 | 11/2005 |
| WO | WO2005115341 | 12/2005 |

* cited by examiner

MICRO-PARTICLE FATTY ACID SALT SOLID DOSAGE FORMULATIONS FOR THERAPEUTIC AGENTS

1. PRIORITY CLAIM

This invention claims priority to Provisional U.S. Patent Application No. 60/494,821, filed on Aug. 13, 2003 by Opawale et al., entitled "Micro-particle fatty acid solid dosage formulations for therapeutic agents," the entire disclosure of which is incorporated herein by reference.

2. FIELD OF THE INVENTION

The invention relates to micro-particle fatty acid salts and their use in pharmaceutical formulations, particularly pharmaceutical formulations for oral delivery of polypeptide drugs.

3. BACKGROUND OF THE INVENTION

The problems associated with oral administration of therapeutic agents such as polypeptides are well known in the pharmaceutical industry and various strategies are being used in attempts to solve them. Delivering therapeutic polypeptides through the gastrointestinal tract is difficult due to the presence of high amounts of polypeptide degrading enzymes in the stomach and the intestine. To achieve oral delivery, the therapeutic polypeptide must both survive the gastrointestinal enzymes and must have an ability to be transported through or around the enterocytes of the intestine.

Examples of approaches to oral delivery include 1) the use of enzyme inhibitors to slow the rate of degradation of polypeptides and polypeptides in the gastrointestinal tract; 2) manipulation of pH to inactivate local digestive enzymes; 3) the use of permeation enhancers to improve the absorption of polypeptides by increasing their paracellular and transcellular transports; 4) the use of nanoparticles as particulate carriers to facilitate intact absorption by the intestinal epithelium, especially, Peyer's patches, and to increase resistance to enzyme degradation; and 5) the use of liquid emulsions to protect the drug from enzymatic degradation in the intestinal lumen.

Oral dosage forms used for delivery of conventional small molecule drugs have also been used in attempts to improve oral delivery of polypeptides. Except for cases where the polypeptide has been chemically modified or where a proprietary absorption enhancer has been used, the results have been disappointing. To the inventors' knowledge, there have been only a handful of human clinical trials demonstrating adequate bioavailability and pharmacokinetics to suggest that commercializing an orally delivered polypeptide is feasible.

There is a need in the art for new approaches to formulating polypeptide drugs for oral delivery that improves upon the current state of the art by enabling larger amounts of drugs to enter the bloodstream through the gastrointestinal tract.

4. SUMMARY OF THE INVENTION

The present invention provides a fatty acid salt composition comprising fatty acid salt particles having a size distribution where a percentage of the particles are from about 1 to about 1,000 microns in diameter. In some embodiments, the fatty acid salt composition can comprise fatty acid salt particles having a size distribution where at least 50% of the particles are from about 5 to about 500 microns and/or having a size distribution where at least 50% of the particles are from about 20 to about 80 microns.

The invention also provides a pharmaceutical composition comprising a fatty acid salt having a size distribution as described herein and a polypeptide drug. In various embodiments, the polypeptide drug can be an unconjugated polypeptide, a pegylated polypeptide, a prodrug and/or a polypeptide conjugated to an oligomer. In additional embodiments, the pharmaceutical composition can comprise a fatty acid salt having a size distribution as described herein and a biologically active agent, which can be a polypeptide, a prodrug, a pure or partial prodrug and/or a small molecule. The biologically active agent can be unconjugated, conjugated to an oligomer and/or pegylated.

6. DEFINITIONS

The terminology used in the description of the invention is for the purpose of describing particular embodiments only and is not intended to be limiting of the invention. As used in the description of the invention and the claims, the singular forms "a," "an," and "the" are intended to include the plural forms as well, unless the context clearly indicates otherwise.

As used herein, the following terms have the meanings indicated:

"Biologically active agent" means a therapeutic or pharmacologic agent that is conjugatable in the manner of the present invention. A biologically active agent can be a small molecule, macromolecule, peptide, protein, or nucleic acid. Examples of biologically active agents include, but are not limited to, those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines;

anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; anti-obesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mineral supplements; mucolytics; narcotics; neuroleptics; neuromuscular drugs; NSAIDS; nutritional additives; peripheral vasodilators; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents. Other non-limiting examples of biological agents include coumarin, insulin, calcitonin, leu-enkephalin, and met-enkaphalin.

"Effective amount" refers to an amount of a compound or composition that is sufficient to produce a desired effect, which can be a therapeutic effect. The effective amount will vary with the age, general condition of the subject, the severity of the condition being treated, the particular biologically active agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000), the entire disclosure of which is incorporated herein by reference).

"Hydrolyzable" means bonds which are subject to hydrolysis under physiological conditions.

"Hydrophilic" means exhibiting characteristics of water solubility, and the term "hydrophilic moiety" refers to a moiety which is hydrophilic and/or which when attached to another chemical entity, increases the hydrophilicity of such chemical entity. Examples include, but are not limited to, sugars and polyalkylene moieties such as polyethylene glycol. "Lipophilic" means exhibiting characteristics of fat solubility, such as accumulation in fat and fatty tissues, the ability to dissolve in lipids and/or the ability to penetrate, interact with and/or traverse biological membranes, and the term, "lipophilic moiety" means a moiety which is lipophilic and/or which, when attached to another chemical entity, increases the lipophilicity of such chemical entity. "Amphiphilic" means exhibiting characteristics of hydropilicity and lipophilicity, and the term "amphiphilic moiety" means a moiety which is amphiphilic and/or which, when attached to a polypeptide or non-polypeptide drug, increases the amphiphilicity of the resulting conjugate, e.g., PEG-fatty acid modifying moiety, sugar-fatty acid modifying moiety.

"Lower alkyl" means substituted or unsubstituted, linear or branched alkyl moieties having from one to six carbon atoms, i.e., $C_1$, $C_2$, $C_3$, $C_4$, $C_5$ or $C_6$. "Higher alkyl" means substituted or unsubstituted, linear or branched alkyl moieties having six or more carbon atoms, e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, etc.

"Monodispersed" describes a mixture of compounds where about 100 percent of the compounds in the mixture have the same molecular weight. "Substantially monodispersed" describes a mixture of compounds where at least about 95 percent of the compounds in the mixture have the same molecular weight. "Purely monodispersed" describes a mixture of compounds where about 100 percent of the compounds in the mixture have the same molecular weight and have the same molecular structure. Thus, a purely monodispersed mixture is a monodispersed mixture, but a monodispersed mixture is not necessarily a purely monodispersed mixture. "Substantially purely monodispersed" describes a mixture of compounds where at least about 95 percent of the compounds in the mixture have the same molecular weight and same molecular structure. Thus, a substantially purely monodispersed mixture is a substantially monodispersed mixture, but a substantially monodispersed mixture is not necessarily a substantially purely monodispersed mixture. The conjugated polypeptides used in the formulations of the invention are preferably monodispersed, substantially monodispersed, purely monodispersed or substantially purely monodispersed, but may also be polydispersed. "Polydispersed" means having a dispersity that is not monodispersed, substantially monodispersed, purely monodispersed or substantially purely monodispersed.

"Polyalkylene glycol" or PAG refers to substituted or unsubstituted, linear or branched polyalkylene glycol polymers such as polyethylene glycol (PEG), polypropylene glycol (PPG), and polybutylene glycol (PBG), and combinations thereof (e.g., linear or branched polymers including combinations of two or more different PAG subunits, such as two or more different PAG units selected from PEG, PPG, PPG, and PBG subunits), and includes the monoalkylether of the polyalkylene glycol. The term PAG subunit means a single PAG unit, e.g., "PEG subunit" refers to a single polyethylene glycol unit, e.g., —($CH_2CH_2O$)—, "PPG subunit" refers to a single polypropylene glycol unit, e.g., —($CH_2CH_2CH_2O$)—, and "PBG subunit" refers to a single polypropylene glycol unit, e.g., —($CH_2CH_2CH_2CH_2O$)—. PAGs and/or PAG subunits also include substituted PAGs or PAG subunits, e.g., PAGs including alkyl side chains, such as methyl, ethyl or propyl side chains, or carbonyl side chains, as well as PAGs including one or more branched forms PAG subunits, such as iso-PPG or iso-PBG.

"Pharmaceutically acceptable" means, with respect to a component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition.

"Polypeptide drug" means a polypeptide having therapeutic activity when administered to a subject or yielding metabolites having therapeutic activity, and derivatives or conjugates of such polypeptides.

"Polypeptide" means a peptide or protein.

"Prodrug" or "pure prodrug" means a biologically active agent that has been chemically derivatized such that, (i) it retains some, all or none of the bioactivity of its parent drug compound, and (ii) it is metabolized in a subject to yield the parent drug compound. In the context of an oligomerized polypeptide prodrug or pure prodrug, the entire oligomer is removed in vivo to yield the biologically active unconjugated polypeptide.

"Treat" or "treating" refers to any type of treatment that imparts a modulating effect, which, for example, can be a beneficial effect, to a subject afflicted with a disorder, disease or illness, including improvement in the condition of the subject (e.g., in one or more symptoms), delay in the progression of the condition, prevention or delay of the onset of the disorder, and/or change in clinical parameters, disease or illness, etc as would be well known in the art, and/or an enhancement to normal physiological functioning.

7. DETAILED DESCRIPTION OF THE INVENTION

The present invention provides micro-particle fatty acid salts and compositions comprising such salts, as well as methods of making and using such salts and compositions. The micro-particle fatty acid salts are particularly useful in the preparation of solid dosage formulations for the oral delivery of therapeutic agents, especially polypeptide drugs, such as polypeptide conjugates. The micro-particle fatty acid salt formulations of the invention are surprisingly able to facilitate the delivery of pharmaceutically effective amounts of polypeptides through the gastrointestinal tract into systemic circulation. Without wishing to be bound by a specific theory, the inventors believe that the micro-particle fatty acid salts rapidly dissolve in the gut to create a microenvironment that protects the polypeptides from enzymatic attack and assists in the transport of the polypeptides through the gut epithelium.

7.1. Micro-Particle Fatty Acid Salts

The invention provides micro-particle fatty acid salts having utility in formulating therapeutic compounds. The inventors have surprisingly discovered that increasing the surface area-to-volume ratio of fatty acid salts, i.e., by reducing the size of the salt particles, dramatically increases their ability to facilitate delivery of polypeptide drugs across the intestinal mucosa. Preferably, the rate of dissolution is higher than the rate of dilution.

Examples of fatty acid salts useful according to the invention include, but are not limited to, short, medium and long chain fatty acids. Some examples of preferred fatty acid salts are medium chain fatty acid salts, such as butyric acid (butanoic acid), caproic acid (hexanoic acid), caprylic acid (octanoic acid), capric acid (decanoic acid), lauric acid (dodecanoic acid), myristic acid (tetradecanoic acid), palmitic acid (hexadecanoic acid), palmitoleic acid (9-hexadecenoic acid), stearic acid (octadecanoic acid), oleic acid (9-octadecenoic acid), linoleic acid (9,12-octadecadienoic acid), alpha-linolenic acid (ALA) (9,12,15-octadecatrienoic acid), gamma-linolenic acid (GLA) (6,9,12-octadecatrienoic acid), arachidic acid (eicosanoic acid), gadoleic acid (9-eicosenoic acid), arachidonic acid (AA) (5,8,11,14-eicosatetraenoic acid), EPA (5,8,11,14,17-eicosapentaenoic acid), behenic acid (docosanoic acid), erucic acid (13-docosenoic acid), DHA (4,7,10,13,16,19-docosahexaenoic acid), lignoceric acid (tetracosanoic acid).

In order to provide an appropriate dissolution-to-dilution ratio, the salts are provided at particle sizes well below currently available particle sizes. The fatty acid salts can be provided in a composition in which at least about 10%, 20%, 30%, 40%, 50%, 60%, 70%, 80%, 90%, 95%, 96%, 97%, 98%, 99% or about 100% of the particles are from about 1 to about 1,000 microns in diameter. The fatty acid salts may be provided in a composition in which at least about 10%, 20%, 30%, 40%, 50%, 60%, 70%, 80%, 90%, 95%, 96%, 97%, 98%, 99% or about 100% of the particles are from about 5 to about 500 microns in diameter. The fatty acid salts may be provided in a composition in which at least about 10%, 20%, 30%, 40%, 50%, 60%, 70%, 80%, 90%, 95%, 96%, 97%, 98%, 99% or about 100% of the particles are from about 10 to about 100 microns in diameter. The fatty acid salts may be provided in a composition in which at least about 10%, 20%, 30%, 40%, 50%, 60%, 70%, 80%, 90%, 95%, 96%, 97%, 98%, 99% or about 100% of the particles are from about 20 to about 80 microns in diameter. Further, The fatty acid salts can be provided in a composition in which the average particle size of the fatty acid salt particles is from about 1 to about 1,000 microns in diameter, preferably about 5 to about 500 microns in diameter, more preferably about 10 to about 100 microns in diameter, ideally about 20 to about 80 microns in diameter.

7.2. Formulations

The micro-particle fatty acid salts of the invention are used in the preparation of solid oral dosage forms, such as tablets and capsules for use in the oral delivery of therapeutic agents. While the present work focuses on the use of these novel formulations for the delivery of polypeptide drugs, it will be appreciated that the formulations are useful for the formulation of small molecule drugs as well. The formulations generally include the micro-particle fatty acid salts of the invention and a pharmaceutical agent such as a polypeptide drug and/or small molecule drug. However, a wide variety of additional excipients can also be included in the formulations of this invention, so long as such excipients do not eliminate the advantageous effects provided by the use of the micro-particle fatty acid salts. The formulations of the invention are particularly useful in the delivery of polypeptide drugs, and especially chemically modified polypeptide drugs, such as conjugated polypeptides.

In some embodiments, the formulations of this invention can comprise a bile salt, which in certain embodiments can be an unconjugated bile salt in which the primary side chain has a single carboxyl group which is at the terminal position and which is unsubstituted (e.g., cholate, ursodeoxycholate, chenodeoxycholate, and deoxycholate). In other embodiments, the formulations of this invention can comprise a conjugated bile salt, which is a bile salt in which the primary side chain has a carboxyl group which is substituted with, for example, an amino acid derivative linked via its nitrogen atom to the carboxyl group (e.g., taurocholate, glycocholate, taurodeoxycholate, and glycodeoxycholate). Mixtures of the various unconjugated and/or conjugated bile salts can also be used.

In other embodiments, the compositions and/or formulations of this invention specifically do not include any bile salt or do not include particular bile salts. For example, the compositions and formulations of this invention can comprise any one or more of the bile salts in any combination and can also exclude one or more other bile in any combination. The formulation of this invention can comprise taurocholate and/or exclude cholate. Any specific bile salt may be included, and any specific bile salt may be specifically excluded, thus, any named combinations of included and excluded bile salts are within the scope of this invention.

A wide variety of optional components known in the art for use in pharmaceutical formulations can also be included in the embodiments of this invention. Examples include, but are not limited to, surfactants, buffer components, coating agents, disintegrates, bulking agents, lubricant components, emulsifying agents, tablet binders, fillers and wetting agents, as are well known in the art.

While optional, surfactants can be useful in the formulations of the invention to increase the solubility of the fatty acids, which can improve the ratio of dissolution to dilution. Examples of useful surfactants include, but are not limited to, acacia, lecithin, sodium lauryl sulfate, glyceral monosterate, mono and di-glycerides, oleic acid, poloxomer, polysorbates, sorbitan esters, and trolamine. When present, surfactants can be included in an amount which is from >0% to about 20% by weight of the pharmaceutical composition. More preferably, surfactants can be included in an amount which is >0% to about 5% by weight of the pharmaceutical composition. Ideally, surfactants are included in an amount which is >0% to about 2% by weight of the pharmaceutical composition.

The formulations of this invention can also include a buffer. Preferred buffers are pharmaceutically acceptable. Buffers utilized in the formulations of the invention preferably have a pH from about 5 to about 10, more preferably greater than 7.0 to about 10.0, even more preferably greater than 7.0 to about 9.0, and ideally about 7.6 to about 8.0. A high pH as described herein has the advantage that it can transiently neutralize the low pH of the stomach and thus deactivate stomach enzymes such as pepsin. Moreover, a high pH buffer system as described herein maintains a favorable pH for the fatty acids in solution. Use of a formulation of this invention creates an environment in the gastrointestinal tract that favors the protection of conjugated or unconjugated polypeptide drugs and enhances the permeability of those polypeptide drugs when combined with the micro-particle fatty acid salts of the invention.

Examples of buffer components suitable for use in the pharmaceutical compositions of the invention include, but are not limited to, acetic acid, ammonium carbonate, ammonium phosphate, boric acid, citric acid, lactic acid, potassium citrate, potassium metaphosphate, potassium phosphate monobasic, sodium acetate, sodium citrate, sodium phosphate dibasic and sodium phosphate monobasic.

In some embodiments, the formulation of this invention is provided in a dosage form, such as a tablet, that is not enterically coated and in some embodiments, the dosage form is enterically coated. In other embodiments, the formulation of this invention does not include a binder and in some embodiments, a binder is included. One or more disintegrants, lubricants, bulking agents, fillers, may or may not be present.

The active ingredients used in the formulations of the inventions can be encapsulated in nanoparticles. Particles in the nanometer size range are absorbed intact by the intestinal epithelium, especially, by Peyer's patches, and travel to sites such as the liver, the spleen, and other tissues. The polypeptide drugs and/or small molecule drugs encapsulated in the nanoparticles can be less sensitive to enzyme degradation. Once in the blood stream, the particles can provide extended release of drug.

7.3. Active Ingredients

Preferred active ingredients are polypeptide drugs. Preferred polypeptide drugs are calcitonin, oligomer-conjugated calcitonin, pegylated calcitonin, brain natriuretic peptide, oligomer-conjugated brain natriuretic peptide, PEGylated brain natriuretic peptide, insulin, oligomer-conjugated insulin, PEGylated insulin, GLP-1, oligomer-conjugated GLP-1, and/or PEGylated GLP-1. One preferred class of drugs are those that are absorbed primarily via the paracellular route.

Other polypeptide drugs useful in the present invention include, but are not limited to, adenosine deaminase, adrenocorticotropic hormone, arginase, arginine deaminease, asparaginase, chymotrypsin, endorphins, enkephalins, erythropoietin, glucagon, glucagon-like peptide-1, growth hormones, hypothalamic releasing factors, insulin, interferon, natriuertic peptides (e.g., brain natriuretic peptide and atrial natriuretic peptide), non-naturally occurring opioids, oxytocin, papain, parathyroid hormone, prolactin, ribonuclease, somatomedin, somatostatin, somatotropin, superoxide dismutase, thyroid stimulating hormones, trypsin, vasopressin, and chemically modified and/or conjugated versions of such polypeptides.

Preferred polypeptides of this invention can have a size in the range of about 300 to about 10,000,000 Daltons, more preferably in the range of about 1,000 to about 50,000 Daltons and ideally in the range of about 1,000 to about 10,000 Daltons.

In a preferred embodiment, the polypeptide drug is a polypeptide coupled to a modifying moiety having a structure selected from the following:

Either of the foregoing moieties may, for example, be coupled to human insulin at a nucleophilic residue, e.g., A1, B1 or B29, or any combination of the foregoing.

In another embodiment, the polypeptide drug is coupled to a modifying moiety having a formula:

$$-X-R^1-Y\text{-PAG-}Z-R^2$$

where,

X, Y and Z are independently selected linking groups and each is optionally present, and X, when present, is coupled to the insulin by a covalent bond, at least one of $R^1$ and $R^2$ is present, and is lower alkyl and may optionally include a carbonyl group, $R^2$ is a capping group, and PAG is a linear or branched carbon chain incorporating one or more alkalene glycol moieties, and optionally incorporating one or more additional moieties selected from the group consisting of —S—, —O—, —N—, and —C(O)—, and where the modifying moiety has a maximum number of 3, 4, 5, 6, 7, 8, 9, 10, 11, 12, 13, 14, 15, 16, 17, 18, 19, 20, 21, 22, 23, 24, or 25 heavy atoms.

In embodiments of the invention, any one or more of X, Y and Z may be absent. Further, when present, X, Y and/or Z may be independently selected from —C(O)—, —O—, —S—, and —N—. In one embodiment, Z is —C(O)—.

In some embodiments, $R^1$ is lower alkyl, and $R^2$ is 0. In other embodiments, $R^2$ is lower alkyl, and $R^1$ is 0.

The modifying moiety may, for example, be coupled to human insulin at a nucleophilic residue, e.g., A1, B1 or B29, or any combination of the foregoing.

In another embodiment, the modifying moiety may include a linear or branched, substituted carbon chain moiety having a backbone of 3-25 atoms selected from the group consisting of —C, —C—, —O—, =O, —S—, —N—, —Si—. The heavy atoms will typically include one or more carbon atoms and one or more non-carbon heavy atoms selected from the group consisting of —O—, —S—, —N—, and =O, preferably —O—, —N—, and =O, more preferably —O— and =O. The carbon atoms and non-carbon heavy atoms are typically present in a ratio of at least 1 carbon atom for every non-carbon heavy atom, preferably at least 2 carbon atoms for every non-carbon heavy atom, more preferably at least 3 carbon atoms for every non-carbon heavy atom. The carbon atoms and oxygen atoms are typically present in a ratio of at least 1 carbon atom for every oxygen atom, preferably at least 2 carbon atoms for every oxygen atom, more preferably at least 3 carbon atoms for every oxygen atom. The modifying moiety may include one or more capping groups, such as branched or linear $C_{1-6}$, branched or linear, or a carbonyl. The modifying moiety will typically include hydrogens, and one or more of the hydrogens may be substituted with a fluorine (which is a heavy atom but should not be counted as a heavy atom in the foregoing formula). The modifying moiety may, for example, be coupled to human insulin at a nucleophilic residue, e.g., A1, B1 or B29, or any combination of the foregoing.

In other embodiments of this invention, the polypeptide drug can be native insulin, an unconjugated, bioactive insulin analog and/or conjugated insulin. In specific embodiments, the polypeptide drug can be the following:

where the —NH— group is the ε-nitrogen of the Lys.

In specific embodiments of this invention, the polypeptide drug can be native calcitonin, an unconjugated, bioactive calcitonin analog and/or conjugated calcitonin. In particular embodiments, the polypeptide drug can be the following:

where the —NH— groups are the ε-nitrogens of the lysines.

Other conjugated polypeptides useful in the formulations of the instant invention are found in the following patents, the entire specifications of which are incorporated herein by reference: U.S. Pat. No. 6,303,569, issued Oct. 16, 2001 to Enzon, Inc., entitled "Trialkyl-lock-facilitated polymeric prodrugs of amino-containing bioactive agents"; U.S. Pat. No. 6,214,330, issued Apr. 10, 2001 to Enzon, Inc., entitled "Coumarin and related aromatic-based polymeric prodrugs"; U.S. Pat. No. 6,113,906, issued Sep. 5, 2000 to Enzon, Inc., entitled "Water-soluble non-antigenic polymer linkable to biologically active material"; U.S. Pat. No. 5,985,263, issued Nov. 16, 1999 to Enzon, Inc., entitled "Substantially pure histidine-linked protein polymer conjugates"; U.S. Pat. No. 5,900,402, issued May 4, 1999 to Enzon, Inc., entitled "Method of reducing side effects associated with administration of oxygen-carrying proteins"; U.S. Pat. No. 5,681,811, issued Oct. 28, 1997 to Protein Delivery, Inc., entitled "Conjugation-stabilized therapeutic agent compositions, delivery and diagnostic formulations comprising same, and method of making and using the same"; U.S. Pat. No. 5,637,749, issued Jun. 10, 1997 to Enzon, Inc., entitled "Aryl imidate activated polyalkylene oxides"; U.S. Pat. No. 5,612,460, issued Mar. 18, 1997 to Enzon, Inc., entitled "Active carbonates of polyalkylene oxides for modification of polypeptides"; U.S. Pat. No. 5,567,422, issued Oct. 22, 1996 to Enzon, Inc., entitled "Azlactone activated polyalkylene oxides conjugated to biologically active nucleophiles"; U.S. Pat. No. 5,405,877, issued Apr. 11, 1995 to Enzon, Inc., entitled "Cyclic imide thione activated polyalkylene oxides"; and U.S. Pat. No. 5,359,030, issued Oct. 25, 1994 to Protein Delivery, Inc., entitled "Conjugation-stabilized polypeptide compositions, therapeutic delivery and diagnostic formulations comprising same, and method of making and using the same," and International Patent Publication No. WO/2004/047871, entitled "Modified naturetic compounds, conjugates, and uses thereof." Additional examples of conjugated polypeptides useful in the formulations of the instant invention can be found in the following U.S. patent applications, the entire specifications of which are incorporated herein by reference: U.S. patent application Ser. No. 09/134,803, filed Aug. 14, 1998; U.S. patent application Ser. No. 10/018,879, filed Dec. 19, 2001; U.S. patent application Ser. No. 10/235,381, filed Sep. 5, 2002; U.S. patent application Ser. No. 10/235,284, filed Sep. 5, 2002; and U.S. patent application Ser. No. 09/873,797, filed Jun. 4, 2001. The present invention specifically contemplates formulations comprising each genus and species of therapeutic compounds described in the foregoing patents and patent applications.

7.4. Preparation of the Formulation

The formulations of the invention are designed to result in rapid dissolution of the fatty acids at the site of absorption. With this goal in mind, the method of making the formulations of this invention generally involves a step of providing fatty acid salts with reduced particle size as described herein.

The formulations of this invention can be processed as a lyophilized powder that includes the micro-particle fatty acid salts of the invention with buffering components.

The formulations of this invention can be processed as a spray dried powder that includes micro-particle fatty acid salts of the invention with or without buffering components and other formulation components.

The formulations of this invention can be processed as a dry granulation or dry powder blend or wet granulation that includes micro-particle fatty acid salts of the invention with or without buffering components and other formulation components.

The fatty acid salts having size ranges according to the invention can be provided by milling using any appropriate equipment as is known in the art to reduce particle size. These finely powdered fatty acids can form the basis of solid oral dosage forms, such as capsules or tablets.

Active ingredients and other components can be combined with the foregoing compositions by methods known in the art.

7.5. Assays

The formulations of the invention preferably have a high dissolution rate. The dissolution rate can be determined as follows: Use USP dissolution apparatus 2 (paddles) at 50 rpm with 500 mL of pH 7.4 phosphate buffer.

USP 26, <711> DISSOLUTION Test Description:

This test is provided to determine compliance with the dissolution requirements where stated in the individual monograph for a tablet or capsule dosage form. Of the types of apparatus described therein, use apparatus 2. For hard or soft gelatin capsules and gelatin-coated tablets that do not conform to the Dissolution specification, repeat the test as follows. Where water or a medium with a pH of less than 6.8 is specified as the Medium in the individual monograph, the same Medium specified may be used with the addition of purified pepsin that results in an activity of 750,000 Units or less per 1000 mL. For media with a pH of 6.8 or greater, pancreatin can be added to produce not more than 1750 USP Units of protease activity per 1000 mL. USP Reference Standards <11> (Dissolution Calibrator, Disintegrating). (Dissolution Calibrator, nondisintegrating) are used to calibrate the equipment.

Apparatus 2: The assembly consists of the following: a covered vessel made of glass or other inert, transparent material; a motor; a metallic drive shaft; and a stirring element. The vessel is partially immersed in a suitable water bath of any convenient size or placed in a heating jacket. The water bath or heating jacket permits holding the temperature inside the vessel at 37±0.5° C. during the test and keeping the bath fluid in constant, smooth motion. No part of the assembly, including the environment in which the assembly is placed contributes agitation, or vibration beyond that due to the smoothly rotating stirring element. An apparatus that permits observation of the specimen and stirring element during the test is preferable. The vessel is cylindrical, with a hemispherical bottom and with the following dimensions and capacities: for a nominal capacity of 1 liter, the height is 160 mm to 210 mm and the inside diameter is 98 mm to 106 mm. The sides are flanged at the top. A fitted cover may be used to retard evaporation.

A shaft and stirring element are fabricated of stainless steel, type 316 or equivalent. The shaft is positioned so that its axis is not more than 2 mm at any point from the vertical axis of the vessel and rotates smoothly and without significant wobble. A speed-regulating device is used that allows the shaft rotation speed to be selected and maintained at the specified stirring rate. A paddle formed from a blade and a shaft is used as the stirring element.

As used herein, the term "high dissolution rate" means that when tested as described herein, the dissolution rate of the fatty acids of this invention in pH 7.4 buffer is fast enough to release at least about 25% of the fatty acids into solution in up to ten minutes. In other embodiments, the dissolution rate can be at least about 30%, 35%, 40%, 45%, 50%, 55%, 60%, 65%, 70%, 75%, 80%, 85%, 90%, 95%, 96%, 97%, 98%, 99% or about 100%, of the fatty acids into solution in up to ten minutes.

7.6. Methods of Treatment

The invention provides a method of treating a subject in need thereof by administering to the subject an effective amount of a formulation of the invention comprising a biologically active agent, such as polypeptide drug, prodrug and/or small molecule. The formulation can be present in a pharmaceutically acceptable carrier.

In particular embodiments, the invention provides methods of treating osteoporosis or pain (e.g., osteoporotic pain or peripheral pain) in a subject in need thereof by orally administering to the subject an effective amount of a formulation of the invention comprising native calcitonin, an unconjugated, bioactive calcitonin analog, conjugated calcitonin and/or the following:

```
Cys Ser Asn Leu Ser Thr Cys Val Leu Gly Lys (NH-

CO(CH2)7(OCH2CH2)7OCH3) Leu Ser Gln Glu Leu His Lys (NH-CO(CH2)7(OCH2CH2)7OCH3) Leu Gln Thr Tyr Pro

Arg Thr Asn Thr Gly Ser Gly Thr Pro.
``` where the —NH— groups are the ε-nitrogens of the lysines.

In other embodiments, the invention provides methods of treating diabetes and/or hyperglycemia in a subject in need thereof, comprising orally administering to the subject an effective amount of a formulation of this invention comprising native insulin, an unconjugated, bioactive insulin analog conjugated insulin and/or Insulin B29 Lys-(NH—CO(CH$_2$)$_5$(OCH$_2$CH$_2$)$_7$OCH$_3$).

where the —NH— group is the ε-nitrogen of the Lys; or an insulin coupled to a modifying moiety having a structure selected from the following:

Either of the foregoing moieties may, for example, be coupled to human insulin at a nucleophilic residue, e.g., A1, B1 or B29, or any combination of the foregoing.

8. EXAMPLES

These techniques have been applied to a variety of native polypeptides and to chemically modified polypeptides.

Figure 1:
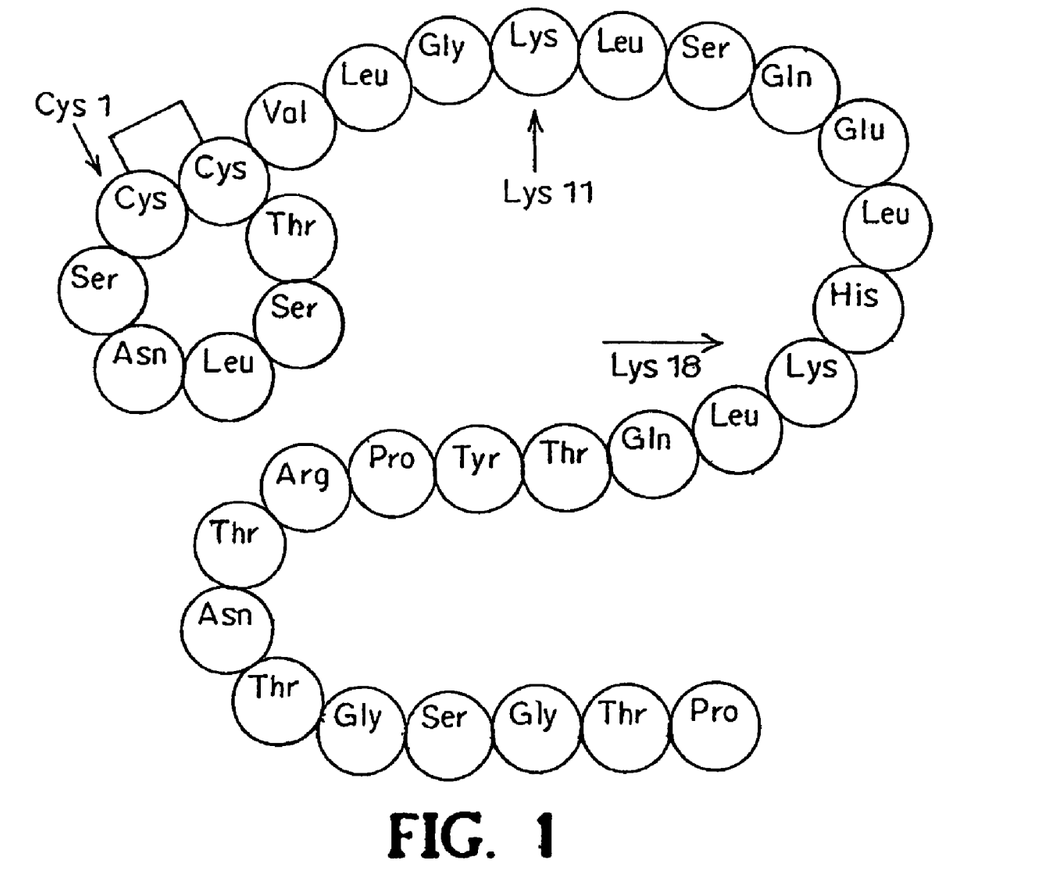
FIG. 1 shows the amino acid sequence and structure of salmon calcitonin.
Figure 2:
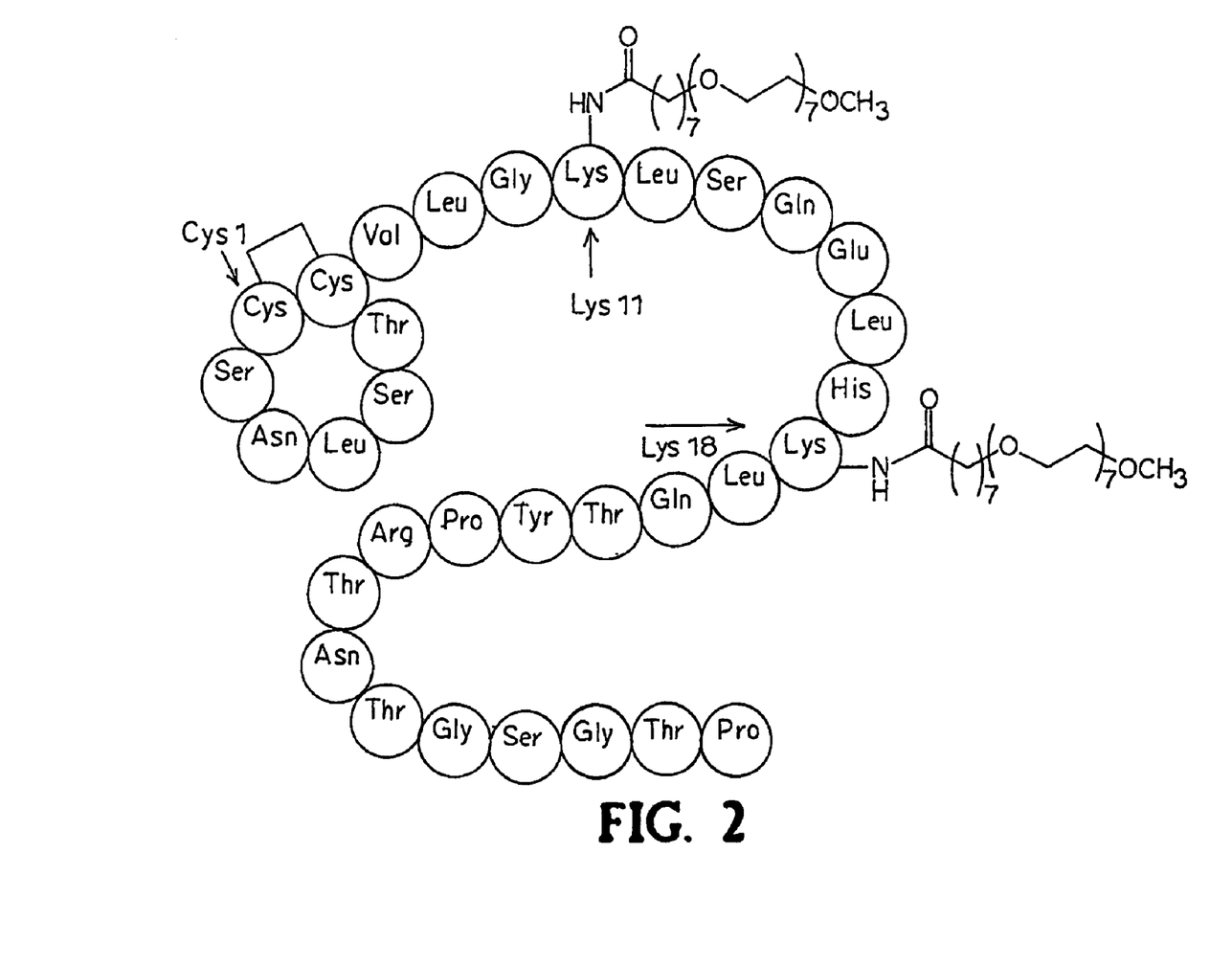
FIG. 2 shows the amino acid sequence and structure of CT-025, a chemically modified form of salmon calcitonin.

8.1. Making the Calcitonin and CT-025 (Modified Calcitonin) Formulations 8.1.1. Milling Sodium Caprate and Sodium Laurate Salmon calcitonin and CT-025 (See FIG. 2) formulations were prepared as follows:

| Excipient | % w/w |
|---|---|
| Sodium Caprate | 53.4% |
| Sodium Laurate | 46.6% |

1. Blend together the sodium caprate and the sodium laurate (preferably at a 1:1 molar ratio).
2. Pass through a jet mill pulverizer to achieve a fine particle size. A fine particle size is a particle size that is less than or falls with the range of 50-100 microns.
3. Resultant material is a premix for subsequent processing 8.1.2. Formulation A

| Excipient | % w/w | mg/tablet |
|---|---|---|
| CT-025 (See FIG. 2) | .036 | .43 |
| Sodium Caprate/Sodium Laurate premix | 50 | 450 |
| Mannitol | 34.5 | 310.5 |
| Sorbitol | 10 | 90 |
| Croscarmellose Sodium | 5 | 45 |
| Sodium Stearyl Fumarate, NF | .5 | 4.5 |
| TOTAL | 100 | 900.43 |

Preparation of Formulation

1. CT-025 (See FIG. 2) is removed from the freezer and allowed to thaw for 1 hour at ambient conditions, and then equilibrated in an open container for an additional 2 hours.
2. Prepare 1% acetic acid solution: pipette 2 mL of glacial acetic acid into a 200 mL QS to volume with purified water and shake well.
3. Weigh out the CT-025 and transfer to a 100 mL Pyrex glass bottle. Add 45 mL of 1% acetic acid solution and swirl to dissolve. This is the granulating solution.
4. Blend together the sodium caprate/sodium laurate; premix with all the mannitol, sorbitol and croscarmellose sodium in a Key granulator with a 5 L bowl.
5. Start the granulator and run the impellor and chopper at appropriate speed to obtain adequate mixing.
6. Add the granulating solution from step 2. Rinse the solution container with 1% acetic acid solution in 10 mL increments to total 60-65 mL of granulating fluid.
7. Granulate for about 20 minutes.
8. Transfer the particles to a tray lined with aluminum foil.
9. Dry the particles in an oven at 37° C. for 16-24 hours. Target moisture is <3%.
10. Pass the dry particles through a #12 sieve.
11. Add the sodium stearyl fumarate and the particles into an 8 quart V-blender. Blend for 2 minutes; then discharge.
12. Using an appropriate tablet press with tooling adequate to make a 900 mg caplet shaped tablet, compress the granulation into tablets.

8.1.3. Formulation B

| Excipient | % w/w | mg/tablet |
|---|---|---|
| CT-025 (see FIG. 2) | .048 | .430 |
| Sodium Caprate/Sodium Laurate premix | 32.94 | 221.17 |
| Mannitol | 46.27 | 310.67 |
| Sorbitol | 13.41 | 90.04 |
| Croscarmellose Sodium | 6.71 | 45.05 |
| Sodium Stearyl Fumarate, NF | .67 | 4.5 |
| TOTAL | 100 | 671.86 |

Preparation of formulation was accomplished as described above.

8.1.4. Formulation C

| Excipient | % w/w | mg/tablet |
|---|---|---|
| CT-025 (see FIG. 2) | .036 | .43 |
| Sodium Caprate/Sodium Laurate premix | 49.55 | 442.0 |
| Mannitol | 34.81 | 310.5 |
| Sorbitol | 10.09 | 90.0 |
| Croscarmellose Sodium | 5.04 | 45.0 |
| Sodium Stearyl Fumarate, NF | .5 | 4.5 |
| TOTAL | 100 | 892.43 |

Preparation of formulation was accomplished as described above.

8.1.5. Formulation D

| Excipient | % w/w | mg/tablet |
|---|---|---|
| Salmon Calcitonin | .036 | 0.37 |
| Sodium Caprate/Sodium Laurate premix | 49.55 | 442.0 |
| Mannitol | 34.81 | 310.5 |
| Sorbitol | 10.09 | 90.0 |
| Croscarmellose Sodium | 5.04 | 45.0 |
| Sodium Stearyl Fumarate, NF | .50 | 4.5 |
| TOTAL | 100 | 892.37 |

Salmon Calcitonin is removed from the freezer and allowed to thaw for 1 hour at ambient conditions, and then equilibrated in an open container for an additional 2 hours, and the formulation is otherwise prepared as described above.

8.1.6. Formulation E (Capsule)

| Excipient | % w/w | mg/tablet |
|---|---|---|
| CT-025 (SEE FIG. 2) | 0 | 0 |
| Sodium Caprate | 23.1 | 155.07 |
| Sodium Laurate | 26.5 | 3.95 |
| Mannitol | 34.8 | 5.18 |
| Sorbitol | 10.1 | 1.50 |
| Croscarmellose Sodium | 5.0 | 0.74 |
| Sodium Stearyl Fumarate, NF | 0.5 | 0.07 |
| TOTAL | 100 | 671.3 |

Preparation of Formulation

1. Blend together the sodium caprate and sodium laurate. Pass through a jet mill pulverizer.
2. Add the premix from step 1 to all the mannitol, sorbitol, croscarmellose sodium and sodium stearyl fumarate; then blend.
3. Fill 671.3 mg of the blend into size 000 hard gelatin capsules.

8.1.7. Formulation F (Capsule) Unmilled

| Excipient | % w/w | mg/tablet |
|---|---|---|
| CT-025 (SEE FIG. 2) | 0 | 0 |
| Sodium Caprate | 23.1 | 155.07 |
| Sodium Laurate premix | 26.5 | 3.95 |
| Mannitol | 34.8 | 5.18 |
| Sorbitol | 10.1 | 1.50 |
| Croscarmellose Sodium | 5.0 | 0.74 |
| Sodium Stearyl Fumarate, NF | 0.5 | 0.07 |
| TOTAL | 100 | 671.3 |

Preparation of Formulation

1. Blend together the sodium caprate and sodium laurate. (Do not mill).
2. Add the premix from step 1 to all the mannitol, sorbitol, croscarmellose sodium and sodium stearyl fumarate; then blend.
3. Fill 671.3 mg of the blend into size 000 hard gelatin capsules.

8.2. Testing the Calcitonin Formulations

Tablet and capsule formulations were prepared using the formulas and processing steps described above. FIGS. 3-8 show dissolution results demonstrating that capric acid sodium salt and lauric acid sodium salt are readily released from various tablet formulations where the fatty acids have been milled to optimum particle size.

Figure 3:
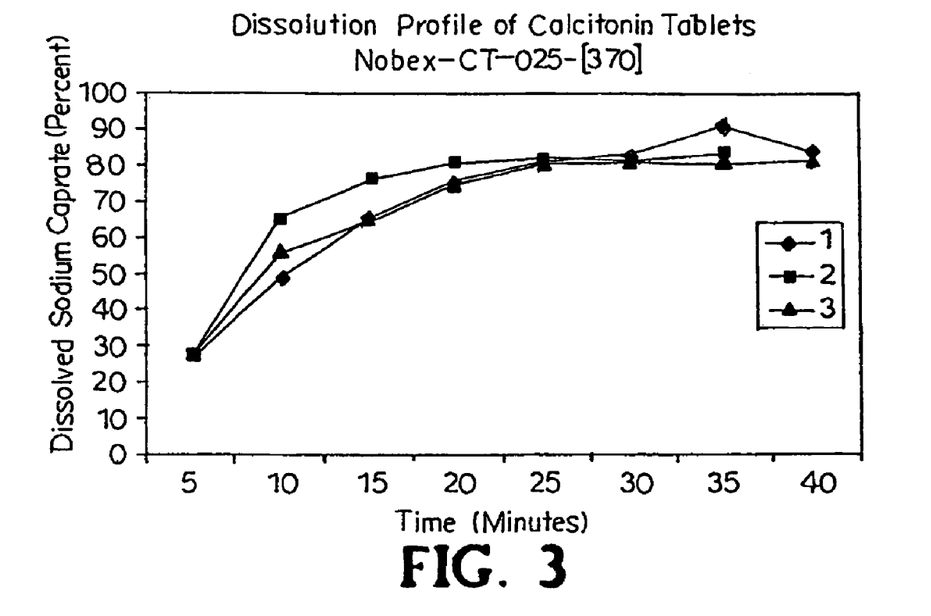
FIG. 3 shows the dissolution of sodium caprate released from three samples of CT-025 (See FIG. 2) tablets of Formula A.

FIG. 3 shows the dissolution of sodium caprate released from three samples of CT-025 (See FIG. 2) tablets of Formula A.

Figure 4:
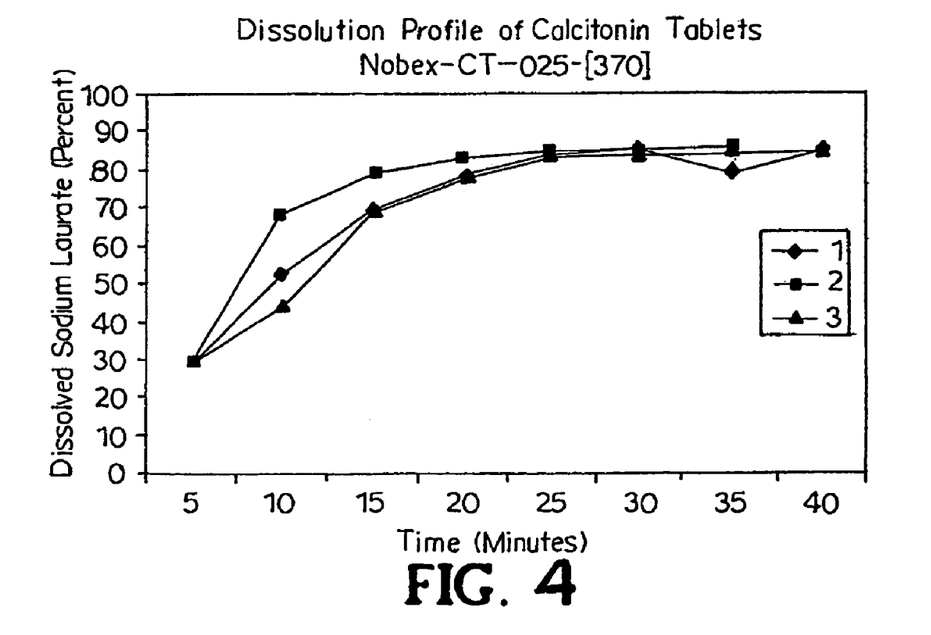
FIG. 4 shows the dissolution of sodium laurate released from three samples of CT-025 tablets of Formula A.

FIG. 4 shows the dissolution of sodium laurate released from three samples of CT-025 tablets of Formula A.

Figure 5:
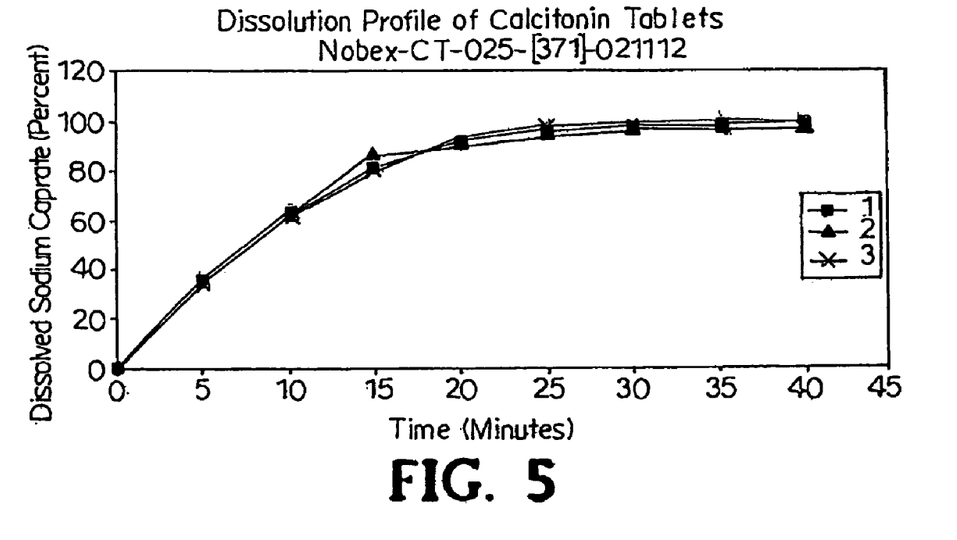
FIG. 5 shows the dissolution of sodium caprate released from three samples of CT-025 tablets of Formula B.

FIG. 5 shows the dissolution of sodium caprate released from three samples of CT-025 tablets of Formula B.

Figure 6:
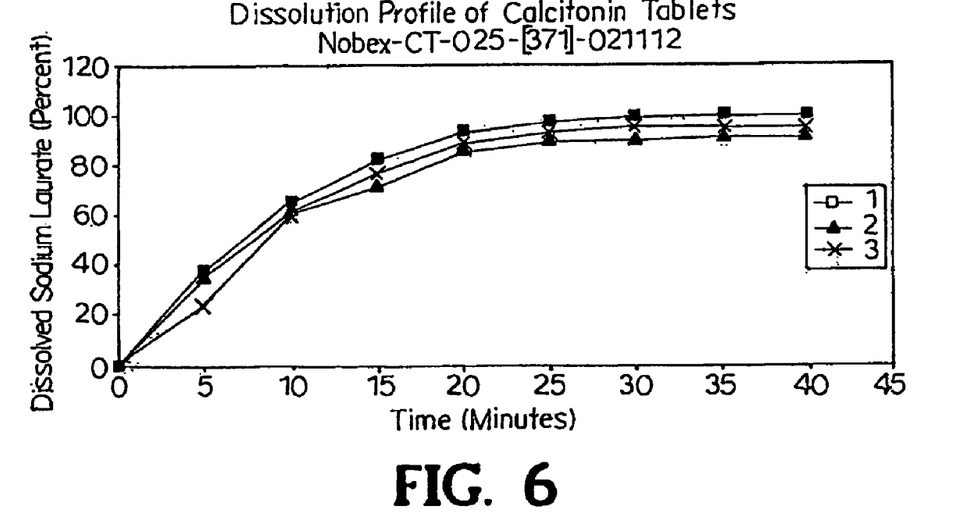
FIG. 6 shows the dissolution of sodium laurate released from three samples of CT-025 tablets of Formula B.

FIG. 6 shows the dissolution of sodium laurate released from three samples of CT-025 tablets of Formula B.

Figure 7:
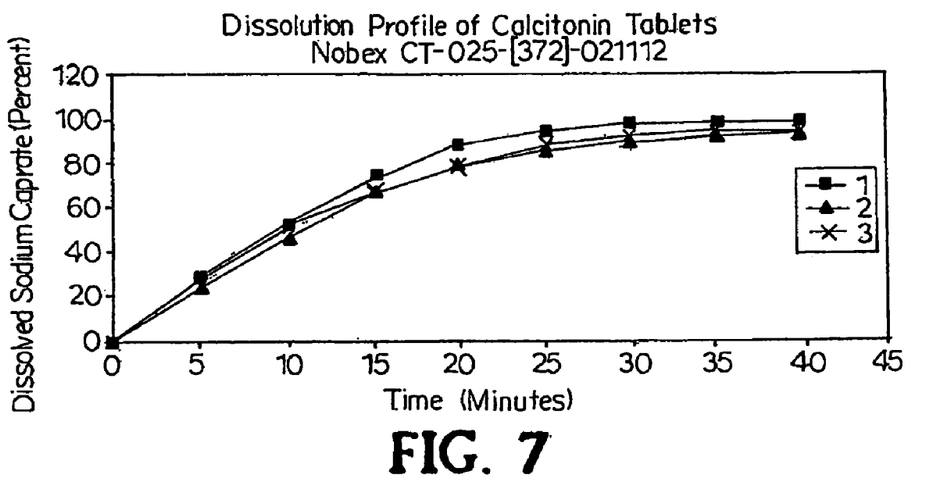
FIG. 7 shows the dissolution of sodium caprate released from three samples of CT-025 tablets of Formula C.

FIG. 7 shows the dissolution of sodium caprate released from three samples of CT-025 tablets of Formula C.

Figure 8:
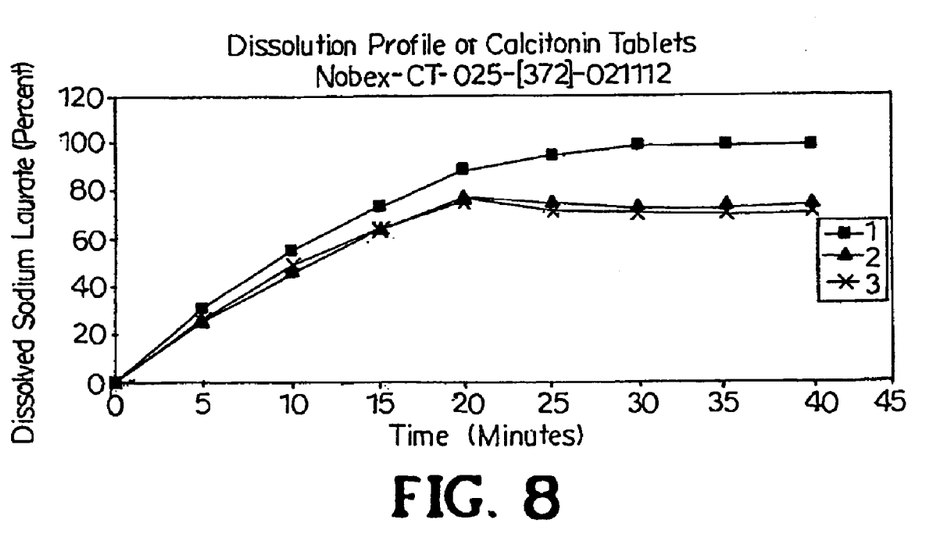
FIG. 8 shows the dissolution of sodium laurate released from three samples of CT-025 tablets of Formula C.

FIG. 8 shows the dissolution of sodium laurate released from three samples of CT-025 tablets of Formula C.

Figure 9:
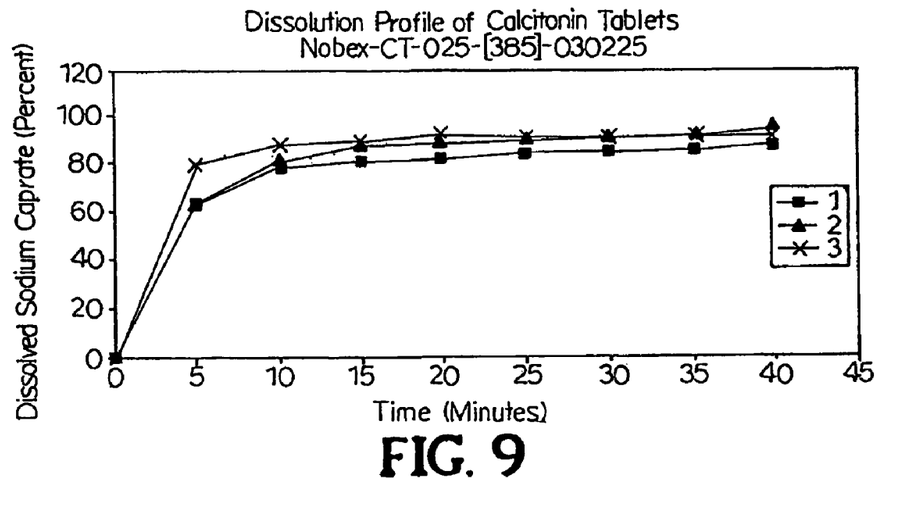
FIG. 9 shows the dissolution of sodium caprate released from six samples of placebo capsules.
Figure 10:
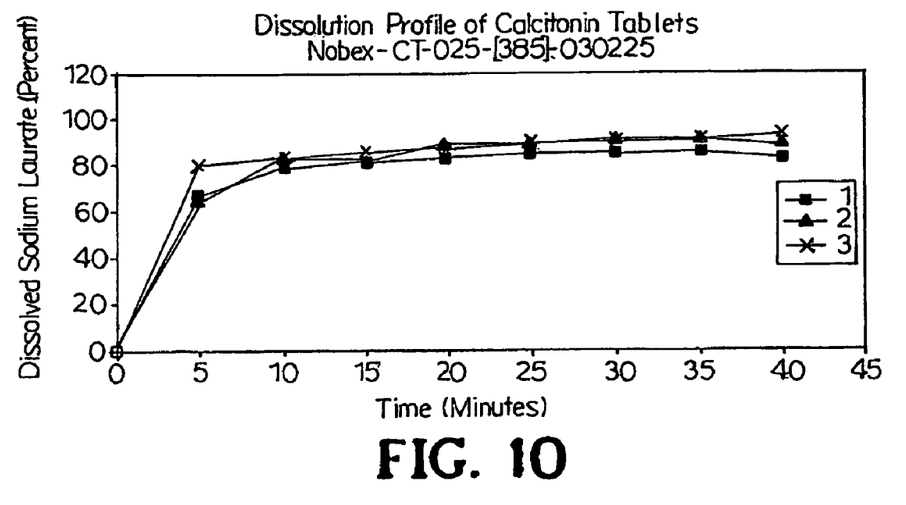
FIG. 10 shows the dissolution of sodium laurate released from six samples of CT-025 capsules.
Figure 11:
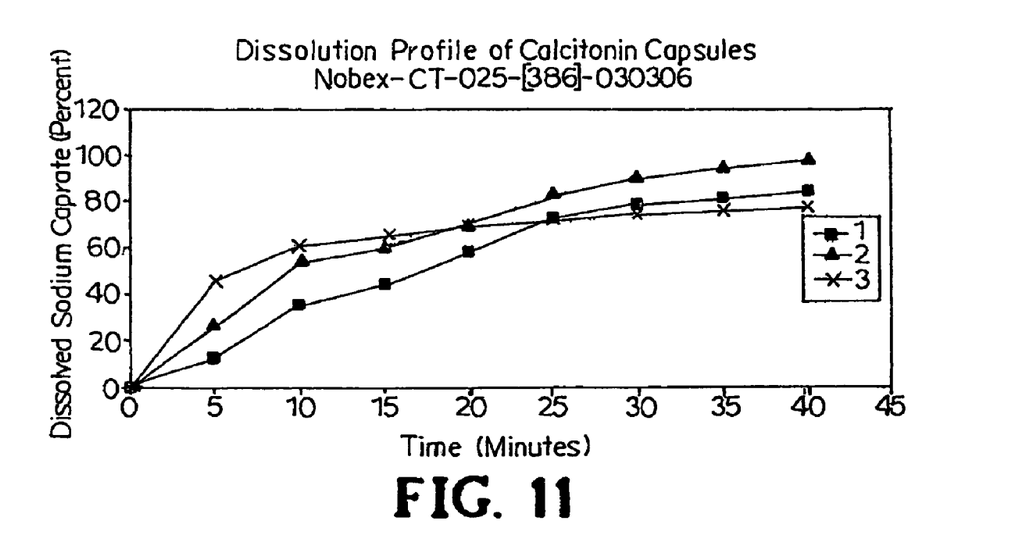
FIG. 11 shows the dissolution of sodium caprate released from six samples of placebo capsules.
Figure 12:
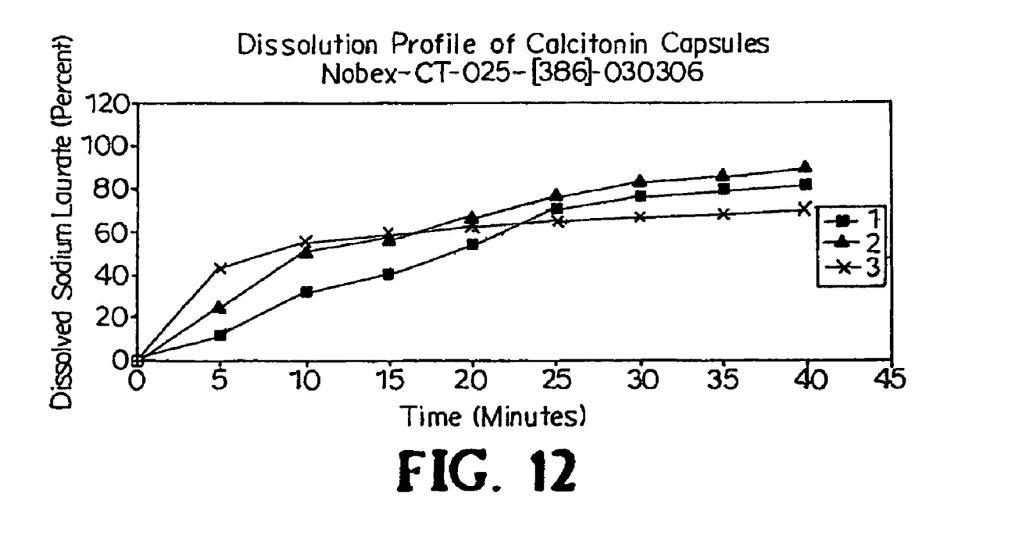
FIG. 12 shows the dissolution of sodium laurate released from six samples of CT-025 capsules.

Capsule formulations were prepared with milled fatty acids (Formula E, FIGS. 9 and 10) and unmilled fatty acids (Formula F, FIGS. 11 and 12). The dissolution results are clearly slower when the fatty acids are not milled. FIG. 9 shows the dissolution of sodium caprate released from three samples of placebo capsules where the fatty acids were milled. FIG. 10 shows the dissolution of sodium laurate released from three samples of CT-025 capsules where the fatty acids were not milled.

FIG. 11 shows the dissolution of sodium caprate released from three samples of placebo capsules. FIG. 12 shows the dissolution of sodium laurate released from three samples of CT-025 capsules.

One tablet containing either CT-025 (320 μg calcitonin equivalents per tablet) (FIG. 13, 371=Formula B; 372=Formula C) or salmon calcitonin (320 μg calcitonin equivalents per tablet) (FIG. 14; 373=Formula D) with the milled fatty acids was dosed to fasted beagle dogs. The dogs were fasted overnight and dosed in the morning. Blood was sampled from the jugular vein at 15, 30, 60, 90 and 120 minutes. Analyses of the blood samples were done to calculate the plasma concentration of either CT-025 or salmon calcitonin in salmon calcitonin equivalents.

Figure 13:
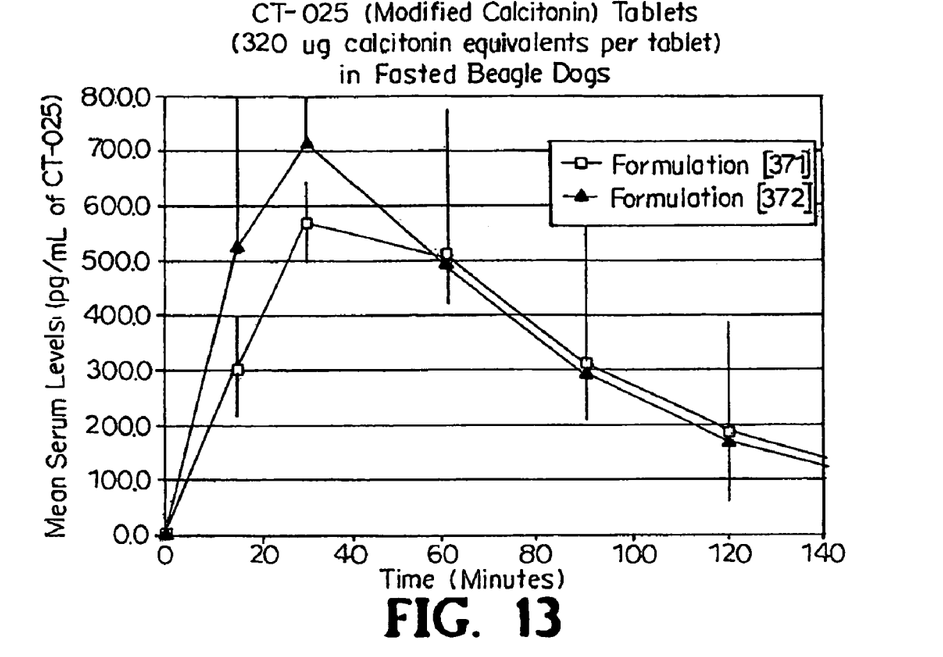
FIG. 13 shows serum plasma levels of CT-025 after oral dosing of fasted beagle dogs with one tablet containing processed fatty acids and 430 µg of CT-025 (equivalent to 320 µg of salmon calcitonin).

FIG. 13 shows serum plasma levels of CT-025 after oral dosing of fasted beagle dogs with one tablet containing processed fatty acids and 430 μg of CT-025 (equivalent to 320 μg of salmon calcitonin).

Figure 14:
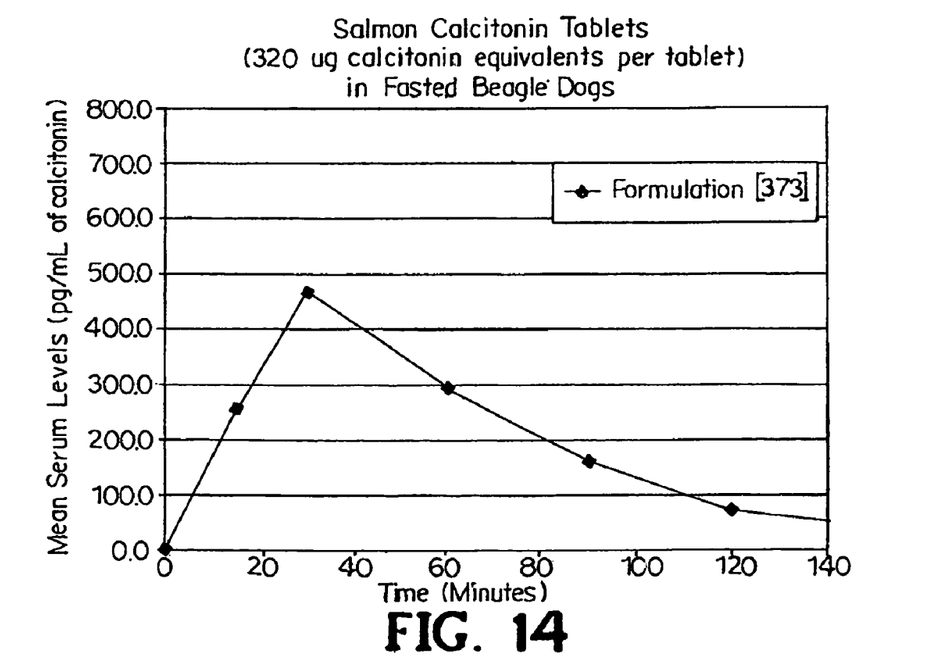
FIG. 14 shows serum plasma levels of salmon calcitonin after oral dosing to fasted beagle dogs with one tablet containing processed fatty acids and 320 µg of salmon calcitonin.

FIG. 14 shows serum plasma levels of salmon calcitonin after oral dosing to fasted beagle dogs with one tablet containing processed fatty acids and 320 μg of salmon calcitonin.

The invention has been described with respect to its preferred embodiments described herein. The invention may be embodied in different forms and should not be construed as limited to the specific embodiments set forth herein. Rather, these embodiments are provided so that this disclosure will be thorough and complete, and will fully convey the scope of the invention to those skilled in the art. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

9. REFERENCES

The entire disclosures of the following references are incorporated herein by reference:

A. T. Florence. The oral absorption of micro- and nanoparticulates: neither exceptional nor unusual. *Pharm. Res.* 14 (1997) 259-266

Ermak et al. Uptake and transport of copolymer biodegradable microspheres by rabbit Peyer's patch M cells. *Cell Tissue Res.* 279 (1995) 433-436

Sakuma et al. Design of nanoparticles composed of graft copolymers for oral polypeptide delivery. *Adv Drug Del Rev.* 47 (2001) 21-37

We claim:

1. A pharmaceutical composition comprising milled fatty acid salt particles having a size distribution wherein the particles are from 50 to 100 microns in diameter, wherein the milled fatty acid salt comprises at least one fatty acid component selected from the group consisting of butyric acid, caproic acid, caprylic acid, capric acid, lauric acid, myristic acid, palmitic acid, and stearic acid, wherein the composition further comprises a pegylated polypeptide drug, wherein the pegylated polypeptide drug is conjugated to an oligomer and wherein the composition is in a solid oral dosage form or as a granulation.

2. The pharmaceutical composition of claim 1, wherein the milled fatty acid salt has a dissolution rate in pH 7.4 buffer of greater than about 50% in up to ten minutes.

3. The pharmaceutical composition of claim 1, wherein the milled fatty acid salt has a dissolution rate in pH 7.4 buffer of greater than about 75% in up to ten minutes.

4. The pharmaceutical composition of claim 1, wherein the milled fatty acid salt has a dissolution rate in pH 7.4 buffer of greater than about 100% in up to ten minutes.

5. The pharmaceutical composition of claim 1, wherein the pegylated polypeptide drug-comprises a prodrug.

6. The pharmaceutical composition of claim 1, wherein the pegylated polypeptide drug comprises native calcitonin or an unconjugated, bioactive calcitonin analog.

7. The pharmaceutical composition of claim 1, wherein the pegylated polypeptide drug comprises conjugated calcitonin.

8. The pharmaceutical composition of claim 1, wherein the pegylated polypeptide drug comprises:

```
                                              (SEQ ID NO: 1)
Cys Ser Asn Leu Ser Thr Cys Val Leu Gly Lys (NH-

CO(CH2)7(OCH2CH2)7OCH3) Leu Ser Gln Glu Leu His Lys (NH-CO(CH2)7(OCH2CH2)7OCH3) Leu Gln Thr Tyr Pro

Arg Thr Asn Thr Gly Ser Gly Thr Pro.
```

9. The pharmaceutical composition of claim 1, wherein the pegylated polypeptide drug comprises native insulin or an unconjugated, bioactive insulin analog.

10. The pharmaceutical composition of claim 1, wherein the pegylated polypeptide drug comprises conjugated insulin.

11. The pharmaceutical composition of claim 1, wherein the pegylated polypeptide drug comprises: Insulin B29 Lys-(NH—CO(CH$_2$)$_5$(OCH$_2$CH$_2$)$_7$OCH$_3$).

12. The pharmaceutical composition of claim 1, wherein the pegylated polypeptide drug comprises an insulin coupled to a modifying moiety having a structure:

coupled to the insulin at a nucleophilic residue.

13. The pharmaceutical composition of claim 1, wherein the pegylated polypeptide drug comprises an insulin coupled to a modifying moiety having a structure:

coupled to the insulin at a nucleophilic residue.

14. The pharmaceutical composition of claim 1, wherein the pegylated polypeptide drug comprises an insulin coupled to a modifying moiety having a structure:

coupled to the insulin at a B29.

15. The pharmaceutical composition of claim 1, wherein the pegylated polypeptide drug comprises an insulin coupled to a modifying moiety having a structure:

coupled to the insulin at B29.

16. The pharmaceutical composition of claim 1, wherein the pegylated polypeptide drug has a molecular weight range of from about 300 to about 10,000,000 Daltons.

17. The pharmaceutical composition of claim 1, wherein the pegylated polypeptide drug has a molecular weight range of from about 1,000 to about 50,000 Daltons.

18. The pharmaceutical composition of claim 1, wherein the pegylated polypeptide drug has a molecular weight range of from about 1,000 to about 10,000 Daltons.

19. The pharmaceutical composition of claim 1, in the form of a tablet wherein the tablet has a dissolution rate of about 30% of the fatty acids into solution in up to ten minutes.

20. The pharmaceutical composition of claim 1, in the form of a tablet wherein the tablet has a dissolution rate of about 95% of the fatty acids into solution in up to ten minutes.

21. The pharmaceutical composition of claim 1, wherein the milled fatty acid salt comprises at least one fatty acid component selected from the group consisting of caproic acid, caprylic acid, capric acid, and lauric acid.

22. A method of treating a subject in need thereof, comprising administering to the subject an effective amount of a formulation comprising the milled fatty acid salt composition of claim 1 and a biologically active agent.

23. A method of treating osteoporosis in a subject in need thereof, comprising administering to the subject an effective amount of the pharmaceutical composition of claim 6.

24. A method of treating diabetes mellitus in a subject in need thereof, comprising administering to the subject an effective amount of the pharmaceutical composition of claim 9.

* * * * *

UNITED STATES PATENT AND TRADEMARK OFFICE
CERTIFICATE OF CORRECTION

PATENT NO. : 7,635,675 B2 Page 1 of 1
APPLICATION NO. : 10/918264
DATED : December 22, 2009
INVENTOR(S) : Opawale et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1312 days.

Signed and Sealed this

Ninth Day of November, 2010

David J. Kappos
*Director of the United States Patent and Trademark Office*

SEQUENCE LISTING

```
<160> NUMBER OF SEQ ID NOS: 1

<210> SEQ ID NO 1
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (11)..(11)
<223> OTHER INFORMATION: ACETYLATION
<220> FEATURE:
<221> NAME/KEY: MOD_RES
<222> LOCATION: (18)..(18)
<223> OTHER INFORMATION: ACETYLATION

<400> SEQUENCE: 1

Cys Ser Asn Leu Ser Thr Cys Val Leu Gly Lys Leu Ser Gln Glx Leu
1               5                   10                  15

His Lys Leu Gln Thr Tyr Pro Arg Thr Asn Thr Gly Ser Gly Thr Pro
            20                  25                  30
```